(12) United States Patent
Imai et al.

(10) Patent No.: US 7,795,438 B2
(45) Date of Patent: Sep. 14, 2010

(54) PROCESSES FOR PRODUCING 1-BENZYL-4-[(5,6-DIMETHOXY-1INDANON)-2-YL]METHYLPIPERIDINE AND HYDROCHLORIDE

(75) Inventors: Akio Imai, Hasaki (JP); Hiroshi Nishimura, Hasaki (JP)

(73) Assignee: Eisai R&D Management Co., Ltd, Tokyo (JP)

( * ) Notice: Subject to any disclaimer, the term of this patent is extended or adjusted under 35 U.S.C. 154(b) by 827 days.

(21) Appl. No.: 10/580,908

(22) PCT Filed: Apr. 27, 2005

(86) PCT No.: PCT/JP2005/008028
§ 371 (c)(1),
(2), (4) Date: May 30, 2006

(87) PCT Pub. No.: WO2005/105742
PCT Pub. Date: Nov. 10, 2005

(65) Prior Publication Data
US 2007/0117846 A1    May 24, 2007

(30) Foreign Application Priority Data
Apr. 28, 2004  (JP) .............................. 2004-133277

(51) Int. Cl.
*C07D 211/32* (2006.01)
(52) U.S. Cl. ...................... 546/206; 546/205
(58) Field of Classification Search ............... 546/205, 546/206
See application file for complete search history.

(56) References Cited

U.S. PATENT DOCUMENTS 4,895,841 A * 1/1990 Sugimoto et al. ...... 514/212.01
7,332,606 B2  2/2008 Imai

FOREIGN PATENT DOCUMENTS

| JP | 01-79151 A | 3/1989 |
| JP | 64-79151 A | 3/1989 |
| JP | 2-169569 A | 6/1990 |
| JP | 02-169569 A | 6/1990 |
| JP | 4-167674 A | 7/1992 |
| JP | 2578475 | 11/1996 |
| JP | 11-171861 | 6/1999 |
| JP | 2965675 | 8/1999 |
| WO | WO 98/39000 | 9/1998 |

OTHER PUBLICATIONS

Iimura et al. "preparation of (-)1-benzyl . . . " CA 118:124398 (1992).*
Cheronis "Semimicro exp. oprg. chjem" p. 31-43 (1958).*
Chen, X., Tetrahedron: Asymmetry, vol. 13, No. 1, 2002, pp. 43-46.
Edited by Shin Ogawara, "Gosei Shiyaku," 1980, Nen, Kodansha Ltd., p. 313.
Edited by Shin Ogawara, "Gosei Shiyaku", Kodansha Ltd., p. 313, (1980).
Chen et at., Tetrahedron: Asymmetry, vol. 13, No. 1, pp. 43-46, (2002).
U.S. Office Action issued on Feb. 14, 2007, U.S. Appl. No. 11/546,444, now U.S. Patent No. 7,332,606.
Supplementary European Search Report issued in European Patent Application No. 05 73 6752 on Apr. 13, 2010.

* cited by examiner

*Primary Examiner*—Celia Chang
(74) *Attorney, Agent, or Firm*—Birch, Stewart, Kolasch & Birch, LLP.

(57) ABSTRACT

Processes for preparing 1-benzyl-4-[(5,6-dimethoxy-lindanon)-2-yl]methylpiperidine (donepezil), which is useful as an intermediate for medicines, and for producing 1-benzyl-4-[(5,6-dimethoxy-1-indanon)-2-yl]methylpiperidine hydrochloride (donepezil hydrochloride), which is useful as a medicine. The process for donepezil hydrochloride production comprises catalytically hydrogenating the compound represented by the structural formula (III) [1-benzyl-4-[(5,6-dimethoxy-lindanon)-2-ylidene]methylpiperidine] with a Raney nickel catalyst under mild conditions and subsequently treating it with hydrochloric acid. Thus, impurities are further diminished. The operations are simple and the process is suitable for industrial production.

12 Claims, No Drawings

PROCESSES FOR PRODUCING 1-BENZYL-4-[(5,6-DIMETHOXY-1INDANON)-2-YL]METHYLPIPERIDINE AND HYDROCHLORIDE

TECHNICAL FIELD

The present invention relates to a process for preparing 1-benzyl-4-[(5,6-dimethoxy-1-indanon)-2-yl]methylpiperidine (hereinafter referred to as a compound of the structural formula (II) or donepezil), which is useful as an intermediate material for medicines, and a process for preparing 1-benzyl-4-[(5,6-dimethoxy-1-indanon)-2-yl]methylpiperidine hydrochloride (hereinafter referred to as a compound of the structural formula (I) or donepezil hydrochloride), which is useful as a medicine. Specifically, the compound of the structural formula (I) can be prepared by catalytically hydrogenating 1-benzyl-4-[(5,6-dimethoxy-1-indanon)-2-ylidene]methylpiperidine (hereinafter referred to as a compound of the structural formula (III)) in the presence of Raney nickel to prepare the compound of the structural formula (II) with high purity, and then reacting the compound of the structural formula (II) with, for example, hydrochloric acid. The compound of the structural formula (I) is effective for treatment, prevention, remission, amelioration, or the like of various types of senile dementia such as, for example, senile dementia of Alzheimer's type; cerebrovascular disorders associated with, for example, apoplexy (encephalorrhagia, brain infarction), cerebral arteriosclerosis, craniocerebral trauma, or the like; and attention deficit, speech disorder, hypobulia, emotional disorder, memory disturbance, hallucinatory-paranoid state, behavioral abnormaly, or the like associated with, for example, postencephalitis, cerebral palsy, or the like.

BACKGROUND ART

A compound of the structural formula (I) and a compound of the structural formula (II) are known compounds. It is known that the compound of the structural formula (II) can be prepared by subjecting a compound of the structural formula (III) or (E)-1-benzyl-4-[(5,6-dimethoxy-1-indanon)-2-ylidene]methylpiperidine to a hydrogenation reaction. It is also known that the compound of the structural formula (I) can be prepared by treating the compound of the structural formula (II) with hydrochloric acid (see, for example, Patent Document 1, Patent Document 2, and Patent Document 3).

Patent Document 1: JP-A-1-79151

Patent Document 2: Japanese Patent No. 2578475

Patent Document 3: JP-A-4-187674

Patent Document 1 discloses a reaction formula as shown below (page 15, lower right column, line 2 to page 16, upper left column, line 1 of the specification).

[Formula 1]

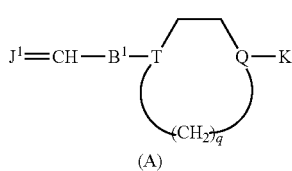

(A)

↓ Reduction

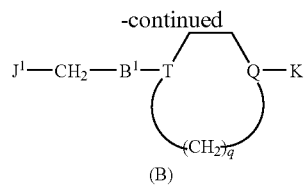

(B)

That is, Patent Document 1 discloses a process for preparing a compound of the formula (B) by reducing a compound of the formula (A) that contains a compound in which $J^1$ is indanone, and describes that "when carrying out catalytic reduction, use of, for example, palladium carbon, Raney nickel, rhodium carbon, or the like as a catalyst leads to a favorable result" (page 16, upper left column, lines 11 to 13 of the specification). Moreover, as a process for preparing donepezil hydrochloride using donepezil as a raw material, a concentrated residue of the compound of the structural formula (II) is dissolved in methylene chloride, and the mixture is treated with 10% hydrochloric acid-ethyl acetate is exemplified (Example 4).

However, Patent Document 1 shows examples of a catalyst to be used in catalytic reduction such as palladium carbon, Raney nickel, rhodium carbon, but does not mention any specific catalytic reduction process. Patent Document 1 only discloses a production example (Example 1) that uses 5% rhodium-carbon as a catalyst, and a production example (Example 4) that uses 10% palladium-carbon as a catalyst. There is no disclosure about a catalytic reduction process using Raney nickel as a catalyst.

Patent Document 2 discloses a reaction formula as shown below (page 3, lines 6 to 8 of the specification).

[Formula 2]

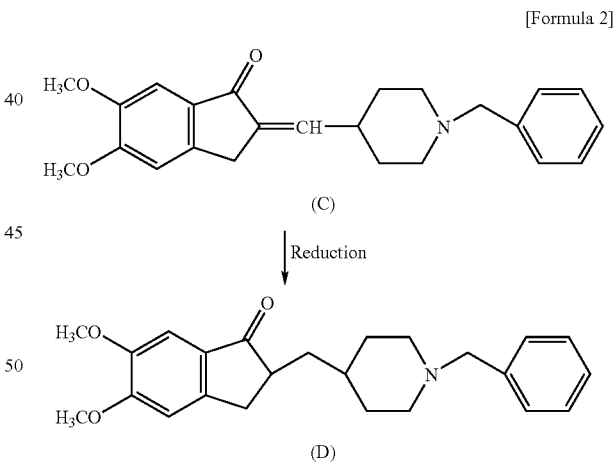

That is, Patent Document 2 discloses a process for preparing a compound of the formula (D) that is a desired substance obtained by catalytically reducing a compound of the formula (C), and describes that "when carrying out catalytic reduction, use of, for example, palladium carbon, Raney nickel, rhodium carbon, or the like as a catalyst leads to a favorable result" (page 3, lower right column, line 6 to line 4 from the bottom of the specification). As a process for preparing donepezil hydrochloride using donepezil as a raw material, a concentrated residue of donepezil is dissolved in methylene chloride, and the mixture is treated with 10% hydrochloric acid-ethyl acetate is exemplified (Production Example 1).

However, Patent Document 2 shows examples of a catalyst to be used in catalytic reduction such as palladium carbon, Raney nickel, rhodium carbon, but does not mention any specific catalytic reduction process. Patent Document 2 discloses a production example that uses 10% palladium-carbon as a catalyst in Production Example 1. There is no disclosure about a catalytic reduction process using Raney nickel as a catalyst.

Patent Document 3 discloses a reaction formula as shown below (page 4, lines 1 to 2 of the specification).

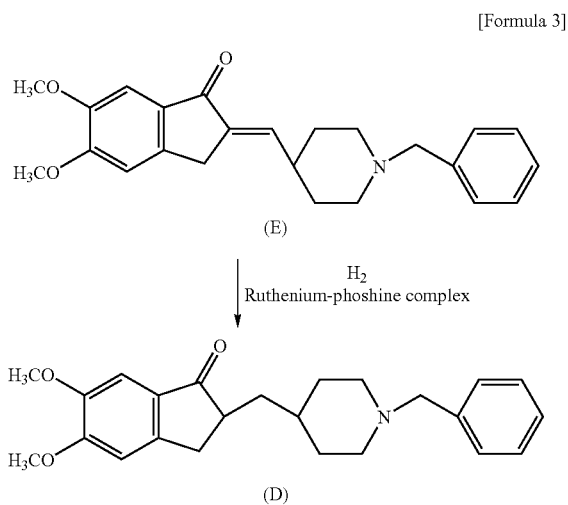

[Formula 3]

That is, Patent Document 3 discloses a process for preparing an optically active compound of the formula (D) by asymmetrically hydrogenating (E)-1-benzyl-4-[(5,6-dimethoxy-1-indanon)-2-ylidene]methylpiperidine represented by the formula (E) in the presence of an optically active ruthenium-phoshine complex catalyst.

In the process of the compound of the structural formula (II) by catalytic hydrogenation in Patent Document 1 and Patent Document 2, a compound of the structural formula (F)

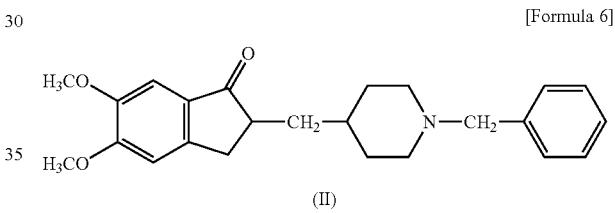

[Formula 4]

is likely to be prepared as a by-product in the catalytic hydrogenation reaction. Therefore, known purification means such as column purification or recrystallization is needed for subjecting the compound of the structural formula (II) to the next reaction. Specifically, catalytic hydrogenation is carried out using 10% palladium-carbon as a catalyst at room temperature and atmospheric pressure for 6 hours, and then a purification step is carried out. That is, following steps are necessary after catalytic hydrogenation: filtering out the catalyst from the reaction solution, distilling off the solvent, purifying the obtained residue by silica gel column chromatography, and concentrating the eluted fraction. However, this process has various problems such as decreasing the yield, and increasing the number of purification operations, and therefore cannot be said to be sufficient as a process for industrially producing the compound of the structural formula (II).

In Patent Document 1 and Patent Document 2, these purification steps aim to remove the above described impurities. However, there is a need for a process for preparing the compound of the structural formula (I) and the compound of the structural formula (II), in which the amount of impurities are decreased more, and which is easily operated and suitable for industrial production.

DISCLOSURE OF THE INVENTION

The present inventors have eagerly studied to solve the above described problems and have found that a process for preparing a compound of the structural formula (II) with high purity, which is easily operated, has a high yield, and is suitable for industrial production by catalytically hydrogenating a compound of the structural formula (III) using a Raney nickel catalyst as a catalyst under mild conditions, thereby completing the present invention. Furthermore, the compound of the structural formula (II) can easily lead to the compound of the structural formula (I) with high purity by converting it into its hydrochloride in a usual manner.

The present invention relates to:

1) A process for preparing a compound [1-benzyl-4-[(5,6-dimethoxy-1-indanon)-2-yl]methylpiperidine] of the structural formula (II):

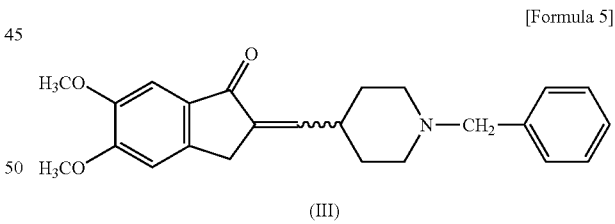

[Formula 6]

characterized by comprising catalytically hydrogenating a compound [1-benzyl-4-[(5,6-dimethoxy-1-indanon)-2-ylidene]methylpiperidine] of the structural formula (III):

[Formula 5]

in the presence of a Raney nickel catalyst;

2) The process according to 1), wherein a reaction solvent for the catalytic hydrogenation is water, an alcohol, acetic acid, an acetic acid ester, an ether, benzene, hexane, toluene, tetrahydrofuran, dioxane, or a mixed solvent thereof;

3) The process according to 1) or 2), wherein a reaction solvent for the catalytic hydrogenation is water, an alcohol, an acetic acid ester, toluene, tetrahydrofuran, or a mixed solvent thereof;

4) The process according to any of 1) to 3), wherein a reaction solvent for the catalytic hydrogenation is water, an alcohol, tetrahydrofuran, or a mixed solvent thereof;

5) The process according to any of 1) to 4), wherein a reaction solvent for the catalytic hydrogenation is tetrahydrofuran or hydrated tetrahydrofuran;

6) The process according to any of 1) to 3), wherein a reaction solvent for the catalytic hydrogenation is toluene, an alcohol, or a mixed solvent thereof;

7) The process according to any of 1) to 6), wherein the catalytic hydrogenation is carried out at a hydrogen pressure of 0.05 to 7.0 MPa;

8) The process according to any of 1) to 7), wherein the catalytic hydrogenation is carried out at a hydrogen pressure of 0.1 to 1.5 MPa;

9) The process according to any of 1) to 8), wherein the catalytic hydrogenation is carried out at a hydrogen pressure of 0.5 to 1.5 MPa;

10) The process according to any of 1) to 9), wherein a weight ratio of the Raney nickel catalyst to the compound of the structural formula (III) is 3 to 30%;

11) The process according to any of 1) to 10), wherein a weight ratio of the Raney nickel catalyst to the compound of the structural formula (III) is 5 to 15%;

12) The process according to any of 1) to 11), characterized in that the catalytic hydrogenation is carried out at a reaction temperature of 4 to 60° C.;

13) The process according to any of 1) to 12), characterized in that the catalytic hydrogenation is carried out at a reaction temperature of 4 to 40° C.;

14) The process according to any of 1) to 13), characterized in that the catalytic hydrogenation is carried out at a reaction temperature of 10 to 25° C.; and 15) A process for preparing a compound of the structural formula (I), characterized by comprising catalytically hydrogenating a compound of the structural formula (III) in the presence of a Raney nickel catalyst to obtain a compound of the structural formula (II), and then treating the compound of the structural formula (II) with hydrogen chloride or hydrochloric acid.

Next, a process for preparing a compound of the structural formula (II) of the present invention will be described in detail.

The compound of the structural formula (II) can be prepared by catalytically hydrogenating the compound of the formula (III) in the presence of a Raney nickel catalyst.

A reaction solvent for the catalytic hydrogenation is not particularly restricted as long as it is applicable to catalytic hydrogenation, but the examples include water, an alcohol, acetic acid, an acetic acid ester, an ether, benzene, hexane, toluene, tetrahydrofuran, dioxane, or a mixed solvent thereof. Among them, preferred solvent is, for example, water, an alcohol, an acetic acid ester, toluene, tetrahydrofuran, or a mixed solvent thereof, or the like. Furthermore, preferred solvent is, for example, water, an alcohol, toluene, tetrahydrofuran, or a mixed solvent thereof, or the like, particularly, for example, water, tetrahydrofuran, toluene, methanol, or a mixed solvent thereof. Tetrahydrofuran, hydrated tetrahydrofuran, and a mixed solvent of tetrahydrofuran and toluene are most suitable. When the above described reaction solvents are specifically illustrated, "alcohol" means, for example, methanol, ethanol, isopropyl alcohol, or the like, "acetic acid ester" means, for example, methyl acetate, ethyl acetate, or the like, and "ether" means, for example, diethyl ether, diisopropyl ether, or the like.

When the catalyst is used as an aqueous suspension of Raney nickel, it is preferable that the suspension is homogeneous with a reaction solvent. The suspension may be a solvent containing, for example, an alcohol or the like that can be homogeneous with water. Solvent substitution of the aqueous suspension of Raney nickel in a usual manner can convert the reaction solvent into, for example, a toluene only or an ethyl acetate only.

The Raney nickel catalyst to be used in the reaction is not particularly restricted, but it may be any of W1 to W8 type.

Commercially available Raney nickel catalysts are provided in a hydrated state, and therefore a weight ratio can be usually determined including a weight of water.

The amount of the Raney nickel catalyst to be used in the reaction is not particularly restricted, but the weight ratio is, for example, in a range of 3 to 30%, preferably in a range of 5 to 20%, and more preferably in a range of 5 to 15% relative to the compound of the structural formula (III), which can be varied appropriately. The weight ratio is usually around 10%. The amount of the solvent to be used is not particularly restricted, but is, for example, 7 to 30 times, and preferably 7 to 10 times of the volume of the compound of the structural formula (III).

Hydrogen to be used in the reaction is not particularly restricted, but the hydrogen pressure is preferably 0.05 to 7.0 MPa, 0.1 to 1.5 MPa, and more preferably 0.5 to 1.5 MPa.

Production of by-products can be further reduced by carrying out the reaction under a lower temperature. For example, the reaction can be carried out at a temperature ranging between 4 and 60° C., but preferably at 40° C. or lower, and particularly suitably at 10 to 25° C. A reaction time varies depending on reduction conditions, but usually the reaction often completes within 4 hours.

After completing the catalytic hydrogenation reaction, the catalyst is filtered out from the reaction solution, and the filtrate is concentrated under reduced pressure. When, for example, an acetic acid ester, an ether, tetrahydrofuran, or the like is used as a solvent for the catalytic hydrogenation reaction, the reaction solvent can be efficiently removed from the concentrated residue by adding, for example, ethanol, or the like, for example, in an amount of 1 to 15 times, and preferably, for example, 1 to 8 times of the volume of the compound of the structural formula (III) to the obtained concentrated residue, and then subjecting the mixture to azeotropy.

The filtrate from which the catalyst was filtered out, or the solution of the concentrated residue to which ethanol was added for azeotropy can be used for a next reaction, for example, a reaction of conversion to hydrochloride using concentrated hydrochloric acid by appropriately distilling off the solvent under reduced pressure, thereby controlling the solvent amount.

The compound of the structure formula (II) can be obtained by distilling off, under reduced pressure, the solvent of the filtrate or the solution that contains ethanol for azeotropy. The compound of the structural formula (II) may be purified by a conventional method such as recrystallization or a column treatment, but may be also used for a next reaction without the purification step.

Next, the process in which the compound of the structural formula (II) is treated with hydrogen chloride or hydrochloric acid to produce the compound of the structural formula (I) will be described.

A reaction solvent for the conversion to hydrochloride is not particularly restricted as long as it is applicable to the conversion of donepezil to its hydrochloride, but the examples include water, an alcohol (methanol, ethanol, or the like), an acetic acid ester, an ether, benzene, hexane, toluene, tetrahydrofuran, dioxane, ketone (acetone or the like), acetonitrile, a halogenated hydrocarbon (chloroform, dichloromethane, or the like), dimethylformamide, dimethylsulfoxide, or the like, or a mixed solvent thereof. Among them, preferred is, for example, an acetic acid ester, ketone, an alcohol, or the like.

Hydrogen chloride or hydrochloric acid for use in the reaction is not particularly restricted, any of concentrated hydrochloric acid, a hydrogen chloride gas, a solvent that has absorbed a hydrogen chloride gas, a mixed liquid of concentrated hydrochloric acid diluted with a solvent may be used. Hydrochloric acid is usually used in an amount of 1 to 2 equivalents, and preferably 1 to 1.2 equivalents relative to 1 equivalent of donepezil. The reaction is carried out by adding hydrochloric acid to the reaction solution containing donepezil usually at 55° C. or lower, and preferably at a range of 10 to 40° C.

Specific examples of a process for preparing the hydrochloride include:

(1) A process in which the catalyst is filtered out from the reaction solution after the catalytic hydrogenation reaction, and then hydrogen chloride or hydrochloric acid is added to the filtrate;

(2) A process in which the catalyst is filtered out from the reaction solution after the catalytic hydrogenation reaction, the filtrate is concentrated, and then hydrogen chloride or hydrochloric acid is added to the prepared solution by dissolving the concentrated residue (donepezil) to the above described solvent;

(3) A process in which the catalyst is filtered out from the reaction solution after the catalytic hydrogenation reaction, the filtrate is concentrated, the concentrated residue (donepezil) is purified from the above described solvent by recrystallization or the like, and then hydrogen chloride or hydrochloric acid is added to the prepared reaction solution by dissolving the purified donepezil to the above described solvent.

The donepezil hydrochloride thus prepared can be recrystallized using the above described solvent. Furthermore, in order to accelerate crystallization, a seed crystal may be used, or a poor solvent may be added to the reaction solution. Examples of the poor solvent include hexane, diethyl ether, and diisopropyl ether. Among them, hexane, diisopropyl ether, or the like is preferred.

According to the present invention, donepezil and donepezil hydrochloride can be prepared industrially in high yield and high purity.

Next, in order to show utility of the present invention, the reaction solutions after the catalytic hydrogenation reaction in Examples and Reference Examples were subjected to HPLC with the following analysis conditions, and purities of donepezil and donepezil hydrochloride were measured based on HPLC relative area values. The results are shown in Table 1.

[Table 1]

TABLE 1

| Test Sample | Hydrogenated reaction solution, Purity (%) | Purity of donepezil hydrochloride or donepezil* (%) |
|---|---|---|
| Example 1 | 99.6 | 99.8 |
| Example 2 | 99.0 | 99.8 |
| Example 3 | 99.1 | 99.7 |

TABLE 1-continued

| Test Sample | Hydrogenated reaction solution, Purity (%) | Purity of donepezil hydrochloride or donepezil* (%) |
|---|---|---|
| Example 4 | 99.4 | 99.8 |
| Example 5 | 99.1 | 99.8 |
| Example 6 | 99.0 | 99.4 |
| Example 7 | 96.5 | 99.0* |
| Example 8 | 95.8 | 98.8* |
| Example 9 | 97.8 | 99.6* |
| Reference Example 1 | 85.8 | N.T. |
| Reference Example 2 | 91.5 | N.T. |
| Reference Example 3 | 75.2 | N.T. |

HPLC Conditions

Detector: UV absorption photometer (Detected wavelength; 271 nm)

Column: Inertsil ODS-2, 4, 6 mm ϕ×150 mm

Mobile phase: Acetonitrile:water:perchloric acid (70%): 1-decanesulfonic acid sodium=350 ml:650 ml:1 ml:2.5 g Flow rate: 1.4 ml/min Column temperature: 35° C.

Sample: Donepezil hydrochloride 10 mg/mobile phase 25 ml

Injecting volume: 20 μl

In the case of a reaction solution, the liquid is adequately diluted and injected-(Example: about 500 times dilution, 10 μl injection).

As apparent from the above described results, donepezil and donepezil hydrochloride prepared by the present invention have good purities, and therefore can be used without a usual purification treatment such as column purification or recrystallization.

BEST MODE FOR CARRYING OUT THE INVENTION

Examples

A compound of the present invention can be prepared, for example, by processes described in following Production Examples and Examples. However, these are only illustrative, and the compounds according to the present invention will not be restricted to the following specific examples in any case.

Example 1

To 741 mL of tetrahydrofuran (hereinafter referred to as THF), 92.1 g of 1-benzyl-4-[(5,6-dimethoxy-1-indanon)-2-ylidene]methylpiperidine and 9 g of Raney nickel were added. The mixture was hydrogenated under stirring at a pressure of 0.10 to 0.40 Mpa and a temperature of 23 to 38° C. for 40 minutes.

After completing the hydrogenation, the catalyst was removed from the reaction solution followed by concentration. To the concentrated residue, 645 ml of ethanol was added to obtain a solution. Subsequently, the solution was crystallized under stirring. Crystallized donepezil was filtered out, and then dried to obtain 76.3 g of donepezil. The obtained donepezil (75.8 g) was dissolved in 606 ml of ethanol. To the reaction solution, 22.8 g of concentrated hydrochloric acid was added under stirring, and the mixture was converted into its hydrochloride. The precipitated crystals were filtered out, and then dried to obtain 80.2 g of donepezil hydrochloride. The values of $^1$H-NMR were consistent with those of Example 3.

Example 2

To a mixed solvent (560 ml of toluene; 140 ml of methanol), 100 g of 1-benzyl-4-[(5,6-dimethoxy-1-indanon)-2-ylidene]methylpiperidine and 10 g of Raney nickel were added. The mixture was hydrogenated under stirring at a pressure of 0.13 Mpa and a temperature of 7 to 8° C. for 4 hours.

After completing the hydrogenation, the catalyst was removed from the reaction solution followed by concentration. To the concentrated residue, 700 ml of ethanol was added to obtain a solution. Subsequently, the solution was crystallized under stirring. Crystallized donepezil was filtered out, and then dried to obtain 76.6 g of donepezil. The obtained donepezil (76.5 g) was dissolved in 612 ml of ethanol. To the reaction solution, 23 g of concentrated hydrochloric acid was added under stirring, and the mixture was converted into its hydrochloride. The precipitated crystals were filtered out, and then dried to obtain 81.1 g of donepezil hydrochloride. The values of $^1$H-NMR were consistent with those of Example 3.

Example 3

To 104 ml of THF, 13 g of 1-benzyl-4-[(5,6-dimethoxy-1-indanon)-2-ylidene]methylpiperidine and 1.3 g of Raney nickel were added. The mixture was hydrogenated under stirring at a pressure of 0.12 Mpa and a temperature of 21 to 25° C. for 2 hours.

After completing the hydrogenation, the catalyst was removed from the reaction solution followed by concentration. To the concentrated residue, 91 ml of ethanol was added to obtain a solution. Subsequently, the solution was crystallized under stirring. Precipitated crystals were filtered out, and then dried to obtain 10.4 g of donepezil. The obtained donepezil (10.3 g) was dissolved in 83 ml of ethanol. To the mixture, 3.1 g of concentrated hydrochloric acid was added under stirring, and the mixture was converted into its hydrochloride. The precipitated crystals were filtered out, and then dried to obtain 10.8 g of donepezil hydrochloride.

$^1$H-NMR (400 MHz, CD$_3$OD) δ(ppm): 1.41-1.51 (3H, m), 1.86-2.10 (4H, m), 2.72-2.76 (2H), 3.04 (2H), 3.28-3.34 (1H, m), 3.49 (2H), 3.85 (3H, s), 3.94 (3H, s), 4.32 (2H, s), 7.05 (1H, s), 7.13-7.14 (1H, s), 7.46-7.53 (5H, m)

Example 4

To 700 ml of THF, 100 g of 1-benzyl-4-[(5,6-dimethoxy-1-indanon)-2-ylidene]methylpiperidine and 10 g of Raney nickel were added. The mixture was hydrogenated under stirring at a pressure of 0.14 Mpa and a temperature of 8 to 10° C. for 4 hours.

After completing the hydrogenation, the catalyst was removed from the reaction solution followed by concentration. To the concentrated residue, 700 ml of ethanol was added to obtain a solution. Subsequently, the solution was crystallized under stirring. Precipitated crystals were filtered out, and then dried to obtain 74.9 g of donepezil. The obtained donepezil (74.8 g) was dissolved in 598 ml of ethanol. To the mixture, 22.5 g of concentrated hydrochloric acid was added under stirring, and the mixture was converted into its hydrochloride. The precipitated crystals were filtered out, and then dried to obtain 78.7 g of donepezil hydrochloride. The values of $^1$H-NMR of donepezil hydrochloride were consistent with those of Example 3.

Example 5

To 104 ml of THF, 13 g of 1-benzyl-4-[(5,6-dimethoxy-1-indanon)-2-ylidene]methylpiperidine and 1.3 g of Raney nickel were added. The mixture was hydrogenated under stirring at a pressure of 1.2 Mpa and a temperature of 21 to 25° C. for 2 hours.

After completing the hydrogenation, the catalyst was removed from the reaction solution followed by concentration. To the concentrated residue, 91 ml of ethanol was added to obtain a solution. Subsequently, the solution was crystallized under stirring. Precipitated crystals were filtered out, and then dried to obtain 10.6 g of donepezil. The obtained donepezil (9 g) was dissolved in 80 ml of ethanol. A mixed liquid of 2.7 g of concentrated hydrochloric acid and 10 ml of ethanol was added to the reaction solution under stirring, and the mixture was converted into its hydrochloride. After adding 135 ml of diisopropyl ether, the precipitated crystals were filtered out, and then dried to obtain 9.5 g of donepezil hydrochloride. The values of $^1$H-NMR of donepezil hydrochloride were consistent with those of Example 3.

Example 6

To a mixed solvent (560 ml of toluene: 140 ml of methanol), 100 g of 1-benzyl-4-[(5,6-dimethoxy-1-indanon)-2-ylidene]methylpiperidine and 10 g of Raney nickel were added. The mixture was hydrogenated under stirring at a pressure of 1.3 Mpa and a temperature of 7 to 8° C. for 4 hours.

After completing the hydrogenation, the catalyst was removed from the reaction solution followed by concentration. To the concentrated residue, 800 ml of ethanol was added to obtain a solution. Subsequently, a mixed liquid of 30.1 g of concentrated hydrochloric acid and 20 ml of ethanol was added to the reaction solution under stirring, and the mixture was converted into its hydrochloride. The precipitated crystals were filtered out, and then dried to obtain 102.8 g of donepezil hydrochloride. The values of $^1$H-NMR of donepezil hydrochloride were consistent with those of Example 3.

Example 7

To 640 ml of methanol, 80 g of 1-benzyl-4-[(5,6-dimethoxy-1-indanon)-2-ylidene]methylpiperidine containing methanol (65 g on a dry basis) and 8 g of Raney nickel were added. The mixture was hydrogenated under stirring at a pressure of 1.2 Mpa and a temperature of 26 to 37° C. for 2 hours.

After completing the hydrogenation, the catalyst was removed from the reaction solution followed by concentration. To the concentrated residue, 390 ml of ethanol was added to obtain a solution. Subsequently, the solution was crystallized under stirring. The precipitated crystals were filtered out, and then dried to obtain 56.0 g of donepezil.

$^1$H-NMR (400 MHz, CD$_3$OD) δ(ppm): 1.23-1.38 (3H, m), 1.50-1.54 (1H, m), 1.66-1.70 (1H, m), 1.77-1.83 (2H, m), 1.99-2.06 (2H, m), 2.66-2.73 (2H, m), 2.88-2.93 (2H, m), 3.22-3.30 (1H, m), 3.51 (2H, s), 3.83 (3H, s), 3.91 (3H, s), 7.03 (1H, s), 7.12 (1H, s), 7.23-7.33 (5H, m)

Example 8

To 520 ml of ethanol, 65 g of 1-benzyl-4-[(5,6-dimethoxy-1-indanon)-2-ylidene]methylpiperidine and 6.5 g of Raney nickel were added. The mixture was hydrogenated under stirring at a pressure of 1.3 to 1.4 Mpa and a temperature of 24 to 42° C. for 2 hours.

After completing the hydrogenation, the catalyst was removed from the reaction solution followed by concentration. To the concentrated residue, 390 ml of ethanol was added to obtain a solution. Subsequently, the solution was crystallized under stirring. The precipitated crystals were filtered out, and then dried to obtain 51.5 g of donepezil. The values of $^1$H-NMR of donepezil were consistent with those of Example 7.

Example 9

To a mixed solvent (520 ml of ethyl acetate: 40 ml of methanol), 65 g of 1-benzyl-4-[(5,6-dimethoxy-1-indanon)-2-ylidene]methylpiperidine and 13 g of Raney nickel were added. The mixture was hydrogenated under stirring at a pressure of 1.4 to 1.5 Mpa and a temperature of 27 to 46° C. for 5 hours.

After completing the hydrogenation, the catalyst was removed from the reaction solution followed by concentration. To the concentrated residue, 390 ml of ethanol was added to obtain a solution. Subsequently, the solution was crystallized under stirring. The precipitated crystals were filtered out, and then dried to obtain 54.3 g of donepezil. The values of $^1$H-NMR of donepezil were consistent with those of Example 7.

Reference Example 1

To 40 ml of THF, 1 g of 1-benzyl-4-[(5,6-dimethoxy-1-indanon)-2-ylidene]methylpiperidine and 0.1 g of 10% palladium carbon were added. The mixture was hydrogenated under stirring at room temperature and atmospheric pressure for 1 hour.

Reference Example 2

To 40 ml of THF, 1 g of 1-benzyl-4-[(5,6-dimethoxy-1-indanon)-2-ylidene]methylpiperidine and 0.1 g of 5% rhodium-carbon were added. The mixture was hydrogenated under stirring at room temperature and atmospheric pressure for 18 hours.

Reference Example 3

To 40 ml of methanol, 1 g of 1-benzyl-4-[(5,6-dimethoxy-1-indanon)-2-ylidene]methylpiperidine and 0.1 g of 5% rhodium-carbon were added. The mixture was hydrogenated under stirring at room temperature and atmospheric pressure for 22 hours.

INDUSTRIAL APPLICABILITY

According to the present invention, donepezil and donepezil hydrochloride can be prepared industrially.

The invention claimed is:

1. A process of preparing a compound [1-benzyl-4-[(5,6-dimethoxy-1-indanon)-2-yl]methylpiperidine] of the structural formula (II):

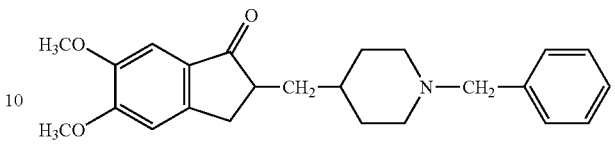

comprising catalytically hydrogenating a compound [1-benzyl-4-[(5,6-dimethoxy-1-indanon)-2-ylidene]methylpiperidine] of the structural formula (III):

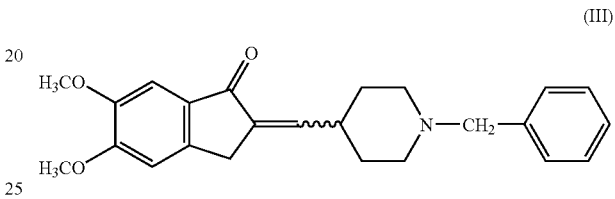

in the presence of a Raney nickel catalyst in a reaction solvent of tetrahydrofuran or a solvent mixture of toluene and methanol, wherein the reaction solvent has a volume 7 to 10 times the volume of the compound of the structural formula (III).

2. The process according to claim 1, wherein the catalytic hydrogenation is carried out at a hydrogen pressure of 0.05 to 7.0 MPa.

3. The process according to claim 1, wherein the catalytic hydrogenation is carried out at a hydrogen pressure of 0.1 to 1.5 MPa.

4. The process according to claim 1, wherein the catalytic hydrogenation is carried out at a hydrogen pressure of 0.5 to 1.5 MPa.

5. The process according to claim 1, wherein a weight ratio of the Raney nickel catalyst to the compound of the structural formula (III) is 3 to 30%.

6. The process according to claim 1, wherein a weight ratio of the Raney nickel catalyst to the compound of the structural formula (III) is 5 to 15%.

7. The process according to claim 1, characterized in that the catalytic hydrogenation is carried out at a reaction temperature of 4 to 60° C.

8. The process according to claim 1, characterized in that the catalytic hydrogenation is carried out at a reaction temperature of about 4 to 40° C.

9. The process according to claim 1, characterized in that the catalytic hydrogenation is carried out at a reaction temperature of 10 to 25° C.

10. A process for preparing a compound [1-benzyl-4-[(5,6-dimethoxy-1-indanon)-2-yl]methylpiperidine hydrochloride] of the structural formula (I):

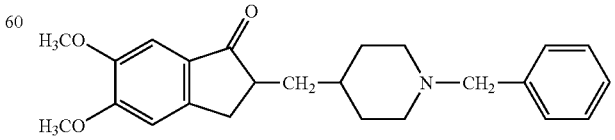

comprising catalytically hydrogenating a compound [1-benzyl-4-[(5,6-dimethoxy-1-indanon)-2-ylidene]methylpiperidine] of the structural formula (III):

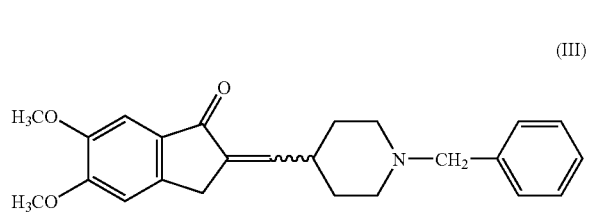

in the presence of a Raney nickel catalyst in a reaction solvent of tetrahydrofuran or a solvent mixture of toluene and methanol, wherein the reaction solvent is has a volume 7 to 10 times of the volume of the compound of the structural formula (III) to obtain a compound [1-benzyl-4-[(5,6-dimethoxy-1-indanon)-2-yl]methylpiperidine] of the structural formula (II):

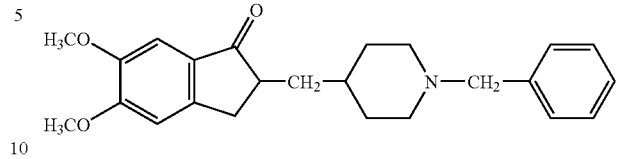

and then treating the compound of the structural formula (II) with hydrogen chloride or hydrochloric acid.

11. The process according to claim 1, wherein the volume ratio of toluene to methanol in the solvent mixture is 4:1.

12. The process according to claim 10, wherein the volume ratio of toluene to methanol in the solvent mixture is 4:1.

* * * * *